United States Patent
Eppstein et al.

[11] Patent Number: 6,022,316
[45] Date of Patent: Feb. 8, 2000

[54] APPARATUS AND METHOD FOR ELECTROPORATION OF MICROPORATED TISSUE FOR ENHANCING FLUX RATES FOR MONITORING AND DELIVERY APPLICATIONS

[75] Inventors: Jonathan A. Eppstein, Atlanta; Michael R. Hatch, Sugar Hill, both of Ga.

[73] Assignees: SpectRx, Inc., Norcross; Altea Technologies, Inc., Atlanta, both of Ga.

[21] Appl. No.: 09/036,169

[22] Filed: Mar. 6, 1998

[51] Int. Cl.[7] ..................... A61B 5/00
[52] U.S. Cl. ............ 600/309; 600/573; 604/19; 604/290
[58] Field of Search .................. 600/309, 345, 600/372, 573, 583; 604/19–21, 27, 28, 289, 290

[56] References Cited

U.S. PATENT DOCUMENTS

| | | |
|---|---|---|
| 5,137,817 | 8/1992 | Busta et al. ............... 435/173 |
| 5,215,520 | 6/1993 | Shroot et al. . |
| 5,273,525 | 12/1993 | Hofmann . |
| 5,318,514 | 6/1994 | Hofmann . |
| 5,445,611 | 8/1995 | Eppstein et al. . |
| 5,458,140 | 10/1995 | Eppstein et al. . |
| 5,462,520 | 10/1995 | Hofmann . |
| 5,547,467 | 8/1996 | Pliquett et al. . |
| 5,749,847 | 5/1998 | Zewert et al. . |
| B1 5,019,034 | 8/1995 | Weaver et al. . |

OTHER PUBLICATIONS

Ultraviolet–Laser Ablation of Skin, Lane et al., *Arch Dermatol*, pp. 609–617, 1985.

Controlled Removal of Human Stratum Corneum by Pulsed Laser, Jacques et al., *J Invest Dermatol*, pp. 88–93, 1987.

*Primary Examiner*—Eric F. Winakur
*Attorney, Agent, or Firm*—Needle & Rosenberg, P.C.

[57] ABSTRACT

An apparatus and a method for electroporating tissue. At least one micropore is formed to a predetermined depth through a surface of the tissue, and electrical voltage is applied between an electrode electrically coupled to the micropore and another electrode spaced therefrom. By applying electroporation to tissue that has been breached by a micropore, the electroporation effects can be targeted at tissue structures beneath the surface, such as capillaries, to greatly enhance the withdrawal of biological fluid, and the delivery for uptake of compounds into the tissue. In a preferred embodiment, a device is provided having elements that are suitable for microporating the tissue and which serve as the electroporation electrodes.

43 Claims, 7 Drawing Sheets

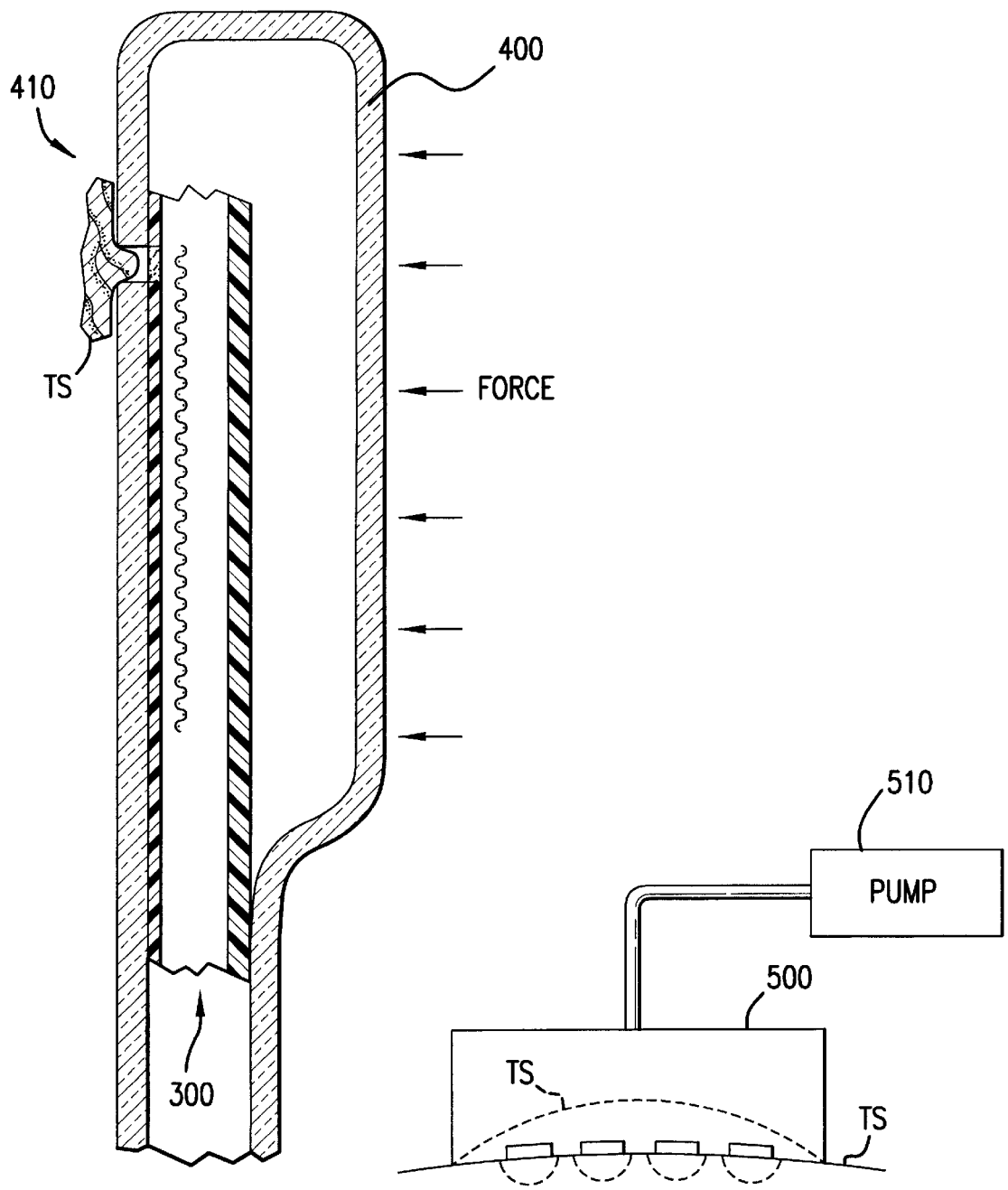

APPARATUS AND METHOD FOR ELECTROPORATION OF MICROPORATED TISSUE FOR ENHANCING FLUX RATES FOR MONITORING AND DELIVERY APPLICATIONS

BACKGROUND OF THE INVENTION

1. Field of the Invention

This invention relates to an apparatus and method for electroporating tissue in which micropores have been formed, for collecting and monitoring biological fluid from the tissue, or for delivery of substances into the tissue.

2. Discussion of the Art

Electroporation of tissue, such as skin, is used to enhance the permeability of the tissue, to facilitate the collection from, or delivery of substances to, the tissue. Electroporation used alone for enhancing the permeability of tissue, such as skin, has limited applications and utility.

Other techniques for enhancing the permeability of tissue surfaces have been developed. One such technology is the microporation of tissue, wherein the tissue surface, such as the skin or mucosal layer, is physically breached by the formation of micropores, approximately 1–1000 µm in diameter. This technology is disclosed in co-pending U.S. patent application Ser. No. 08/776,863, filed Feb. 7, 1997, and entitled "Microporation Of Human Skin For Drug Delivery and Monitoring Applications," the entirety of which is incorporated herein by reference.

Microporation of tissue, such as skin, has been proven significantly effective in the collection of fluids, such as interstitial fluid, for the purposes of quantitating an analyte in the interstitial fluid.

There is, however, room for improving and enhancing the capabilities of microporation and electroporation. In particular, it is desirable to combine the benefits of electroporation and microporation.

SUMMARY OF THE INVENTION

Briefly, the present invention is directed to an apparatus and method for electroporating tissue. At least one micropore is formed to a predetermined depth through a surface of the tissue; first and second electrodes are positioned spaced apart on the tissue and one of the electrodes is electrically coupled to the at least one micropore; and an electrical voltage is applied between the electrodes to produce a desired electroporation in the tissue between the electrodes. The electroporation electrodes may also serve the function of participating in the microporation of the tissue. In accordance with a preferred embodiment, a device having elements that are suitable for microporating the tissue and electroporating the tissue is provided.

By microporating the tissue prior to the application of electroporation, the parameters for electroporation can be significantly adjusted and the sensation to the patient can also be reduced. Furthermore, by first breaching the surface of the tissue with micropores, the electroporation can be directed at selected structures in the skin tissue matrix, such as capillaries, vessels, lymphatic paths and the like, so as to enhance the forcing function of interstitial fluid from the microporated tissue, thereby facilitating the collection and analysis of the fluid. In addition, electroporation applied to the capillaries also increases the capillary permeability to substances which are to be delivered into the tissue.

The above and other objects and advantages of the present invention will become more readily apparent when reference is to made to the following description, taken in conjunction with the accompanying drawings.

BRIEF DESCRIPTION OF THE DRAWINGS

FIG. 6 is a side view of a mechanical device suitable for deforming the surface of tissue to enhance the effects of electroporation.

FIG. 7 is a schematic diagram showing the use of a suction device to enhance the effects of electroporation.

DETAILED DESCRIPTION OF THE DRAWINGS

Definitions

Figure 1:
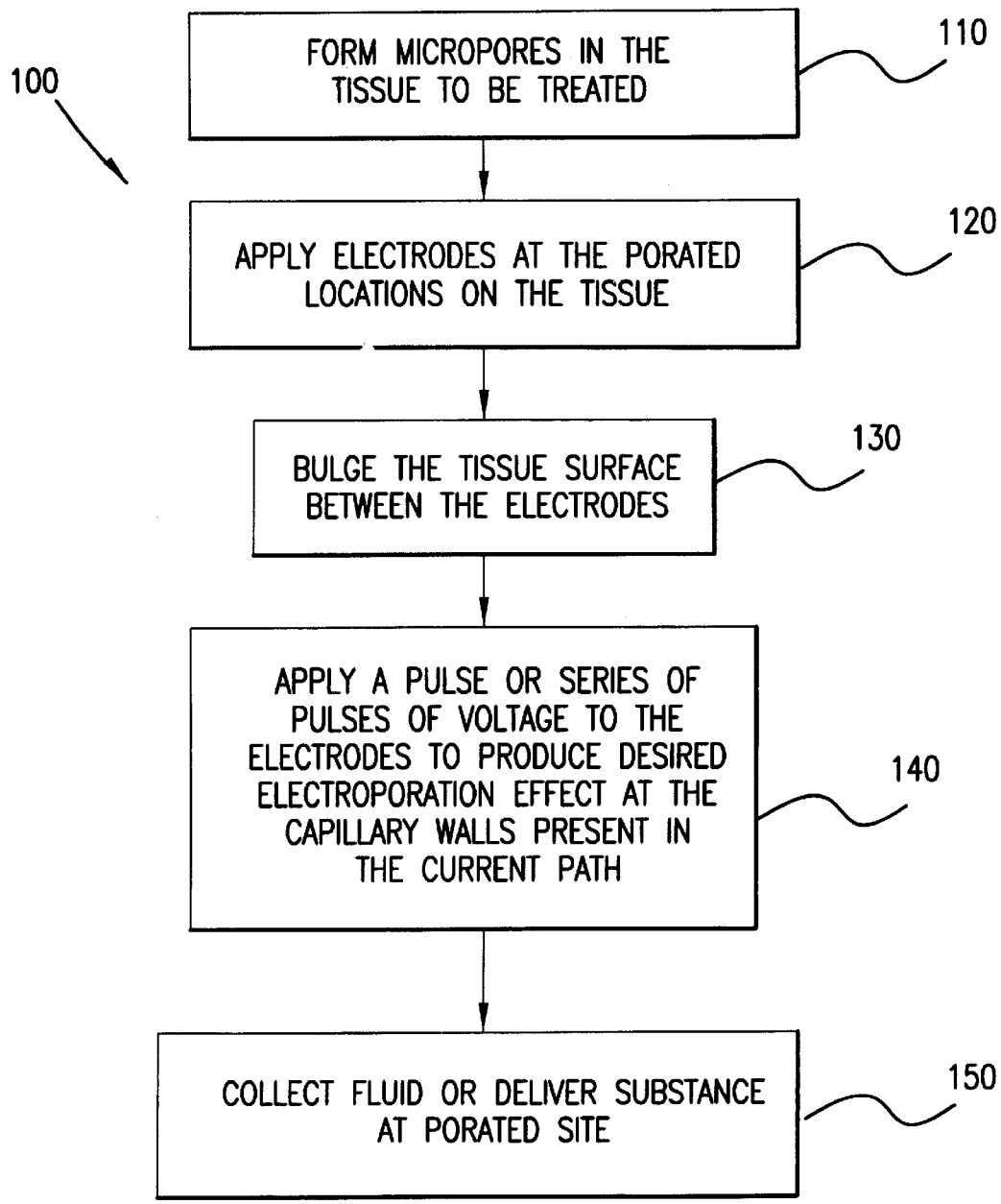
FIG. 1 is a flow chart generally depicting the overall process employing microporation and electroporation of tissue in accordance with the present invention.

As used herein, the expression "biological fluid" is intended to include "interstitial fluid" (ISF), which is the clear fluid that occupies the space between the cells in the body. The term "stratum corneum" means the outermost layer of the skin, consisting of from about 15 to about 20 layers of cells in various stages of drying out. The stratum corneum provides a barrier to the loss of water from inside the body to the external environment and from attack from the external environment to the interior of the body. The term "epidermis" means the region of the skin including the stratum corneum and extending approximately 10 times as thick as the stratum corneum into the body, wherein the portions of the epidermis beneath the stratum corneum is comprised of living, metabolically active cells. The epidermis does not contain capillaries or blood vessels. The term "dermis" means the region of skin approximately 10 times as thick as the epidermis and found just below the epidermis. The dermis contains large amounts of collagen, which provides structural integrity to the skin. The dermis contains a layer of small blood vessels and capillaries that provide oxygen and nutrients to the rest of the layers of skin.

As used herein, the term "tissue" means an aggregate of cells of a particular kind, together with their intercellular substance, that form a structural material of an animal or plant. At least one surface of the tissue must be accessible to electromagnetic radiation so that the invention can be carried out. The preferred tissue is the skin. Other tissues suitable for use with this invention include mucosal tissue and soft organs.

As used herein, "poration," "microporation," or any such similar term means the formation of a small hole or pore to a desired depth in or through the biological membrane, such as skin or mucous membrane, or the outer layer of an organism to lessen the barrier properties of this biological membrane to the passage of biological fluids, such as analytes from below the surface for analysis or the passage of permeants or drugs into the body for selected purposes, or for certain medical or surgical procedures. Preferably the hole or micropore will be no larger than about 1 mm (1000 µm) in diameter, and will extend to a selected depth, as described hereinafter.

As used herein, "biological membrane" or "membrane" means any tissue material present within a living organism forming a barrier between distinct tissues or areas of an organism, or between tissue of an organism and the external environment, and includes without limitation: the skin, mucosal membranes; buccal membranes; the outer layers of a plant; and the walls of a cell or a blood vessel.

"Electroporation" means a process by which electrical current is applied through tissue by electrodes spaced apart on or in the tissue to temporarily increase the permeability of the tissue membranes to collection of fluids therefrom, or delivery of permeants thereto. It involves the delivery of pulses of electrical energy of relative short duration to cause the voltage potential developed across the targeted tissue structure to be sufficiently greater than a threshold level to produce the desired electroporation. The parameters typical of electroporation and the thresholds for effective operation under many operating conditions are well known in the art, and are discussed in several articles, including "Electroporation Of Mammalian Skin: A Mechanism to Enhance Transdermal Drug Delivery," *Proc. Nat'l Acad. Sci.,* 90:1054–1058 (1993) by Prausnitz et al., and "Methods For In Vivo Tissue Electroporation Using Surface Electrodes," *Drug Delivery,* 1:1265–131 (1993) by Prausnitz et al.

As used herein, "micropore" or "pore" means an opening formed by the microporation method.

As used herein, the term "bioactive agent," "permeant," "drug," or "pharmacologically active agent" or "deliverable substance" or any other similar term means any chemical biological material or compound suitable for delivery by the methods previously known in the art and/or by the methods taught in the present invention, that induces a desired effect, such as a biological or pharmacological effect, which may include but is not limited to (1) having a prophylactic effect on the organism and preventing an undesired biological effect such as preventing an infection, (2) alleviating a condition caused by a disease, for example, alleviating pain or inflammation caused as a result of disease, (3) either alleviating, reducing, or completely eliminating the disease from the organism, and/or (4) the placement within the viable tissue layers of the organism of a compound or formulation which can react, optionally in a reversible manner, to changes in the concentration of a particular analyte and in so doing cause a detectable shift in this compound or formulation's measurable response to the application of energy to this area which may be electromagnetic, mechanical or acoustic.

The term "heated probe" means a probe, preferably solid phase, which is capable of being heated in response to the application of electrical or electromagnetic (optical) energy thereto. For simplicity, the probe is referred to as a "heated probe" which includes a probe in a heated or unheated state, but which is heatable.

The present invention is directed to creating an electroporation effect to selectively enhance the permeability of selected structures within tissue, including but not limited to, cell membrane walls, the membranes separating different tissue types and the walls of the capillaries and blood vessels present in the dermis, to allow a greater out-flux of the aqueous fluid from within the blood volume into the interstitial spaces or to allow a greater influx of a compound introduced into these surrounding tissues and hence the blood stream. This method may be used in conjunction with additional permeation enhancement measures of the skin tissues to facilitate the external collection of a volume of interstitial fluid sufficient to allow an assay to be run on the interstitial fluid for the quantification of a selected analyte, such as glucose, or for the delivery of a permeant into the body.

It is known that the physical size of the capillary and vessel cross-section is several times larger than the dermal and epidermal cells also present in the current path, and the potential drop across all of these structures is known to occur almost exclusively at the outer membrane, or in the case of the capillaries or blood vessels, at the epithelial cell layer comprising the main barrier structure within the wall of the capillary or vessel. Consequently, a current density sufficient to produce a potential drop exceeding the nominal threshold (preferably greater than about 1 volt) to achieve electroporation across the epithelial cell layer is not sufficient to electroporate the membranes present in other tissue structures, such as the cell walls of the epidermal cells, through which the current is flowing, hence allowing a selective electroporation of only the targeted membranes.

FIG. 1 depicts the steps of the overall process 100 according to the present invention. Various devices and techniques for performing each of the steps in FIG. 1 are shown and described hereinafter. Briefly, the overall process involves forming at least one micropore to a predetermined depth range through a surface of the tissue; positioning at least a first electrode electrically coupled to the at least one micropore and a second electrode spaced apart from the first electrode; applying an electrical voltage between the first and second electrodes sufficient to produce a desired electroporation in the tissue present in the induced current path.

Step 110 involves forming micropores in the tissue to be treated. At least one micropore is formed, though as will become more apparent hereinafter, multiple micropores may be formed. The micropore is formed through a surface of the tissue, such as skin, to a predetermined depth range into the tissue. For example, at least one microporation in the outer layer of the epidermis is formed to allow the high impedance layer of the stratum corneum to be eliminated from the current path. The depth to which a micropore is created is described in co-pending U.S. Provisional Application Ser. No. 60/077,135, Attorney Docket No., filed on even date, and entitled "Integrated Poration, Harvesting and Analysis Device, and Method Therefor," the entirety of which is incorporated herein by reference. In addition, microporation depth control is also described in co-pending U.S. application Ser. No. 09/036,053 entitled "Method and Apparatus For Enhancing Flux Rates Of A Fluid In A Microporated Biological Tissue," Attorney Docket No., filed on even date, the entirety of which is incorporated herein by reference.

Preferably, at least two micropores are formed some distance apart in the locations where the electrodes are to be placed. These micropores are created by one of the several methods such as those disclosed in the aforementioned co-pending U.S. application Ser. No. 08/776,863, and described hereinafter. The micropores range in size from 1 to 1000 microns across and from 20 to 1000 microns deep, but preferably 80 to 500 microns across and 40 to 180 microns deep.

Next, in step 120, electrodes are applied or positioned (if not already in position) about the microporation(s) on the tissue. This step involves the mechanical positioning of at least first and second electrodes such that at least one of the electrodes is electrically coupled to the micropore. That is, at least one of the electrodes (i.e., the first electrode) is positioned proximate the micropore so that the dominant or preferred current path to that electrode, induced by the electrical voltage between it and the second electrode is through the micropore. This assists in ensuring that at least some, if not the preferred, current density paths through the tissue intersects at least some of the capillary loop structures and blood vessels present in these tissues. The second electrode can be coupled to any other tissue surface, acting to complete the current path through the tissue with respect to the first electrode.

On the other hand, each of the first and second electrodes may be electrically coupled to micropores formed in the tissue separated from each other. The electrodes may electrically penetrate into the micropore through a compliant electrolyte, e.g., a conductive hydrogel or a saline solution, placed on the contacting surface to facilitate electrical contact into the micropores. Additionally, according to a preferred embodiment, the same elements that are used to thermally microporate the tissue are used as electroporation electrodes after the thermal microporation process has been completed.

Step 130, an optional step, involves deforming the tissue surface so that it bows or bulges between the microporations. Depending on the depth of the micropores and the penetration of the electrode into them, a small deformation of the tissue surface into a bowed shape is created between the micropores such that a line drawn between the micropores would intersect the targeted tissue structures, such as capillaries and vessels in, for example, the dermis.

Next, in step 140, an electrical voltage pulse or series of voltage pulses is applied between the first and second electrodes of sufficient magnitude or amplitude such that the resulting current flow through the intervening tissue, including the targeted structures causes a potential drop across these targeted tissue structures, such as capillary walls, which exceeds the electroporation threshold for these tissue structures present in the current path. The pulsing scheme can include the modulation of pulse amplitude, pulse timing, pulse polarity and geometrical direction of the pulses to achieve desired electroporation effects. The duration of the pulse is relatively short, such as (1 $\mu$s to 10 ms) with an amplitude designed to ensure that the potential drop across the targeted membrane structures in the current path nominally exceeds a 1 volt potential, the value known in the art as being the nominal threshold level at which effective poration of a membrane begins to occur. The pulse duration and amplitude applied to the electrodes depends on the specific tissue to which the electrodes are applied, the spacing between the electrodes, and other parameters that affect the impedance of the current path and the coupling of the electrodes to the tissue.

In step 150, biological fluid exuded from the microporated and electroporated tissue is collected for analysis, or a substance, such as a drug or other bioactive agent is delivered into the permeability-enhanced tissue.

Figure 2A:
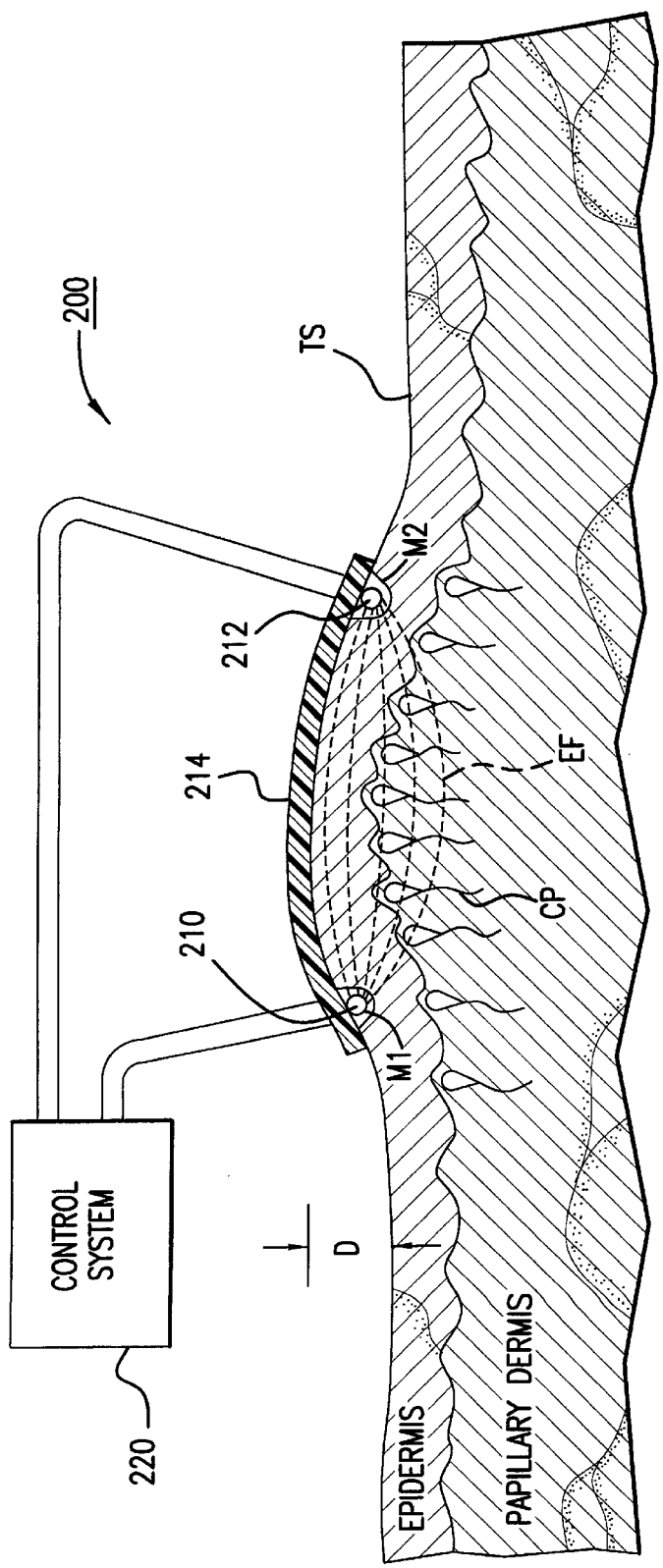
FIG. 2A is a schematic diagram of an apparatus for electroporating tissue according to the present invention.
Figure 2B:
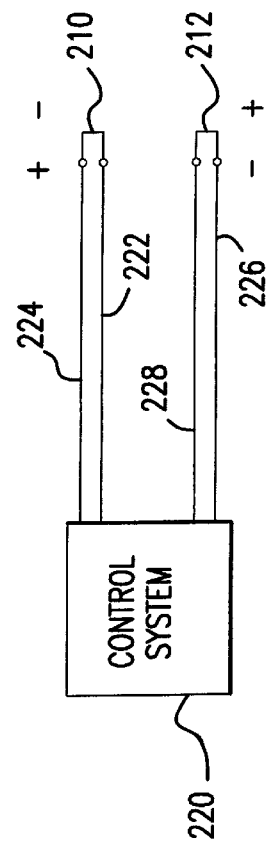
FIG. 2B is a schematic diagram showing the coupling of electrical current for microporation and electrical voltage for electroporation are supplied to combination electrical heated probes/electroporation electrodes.

Turning to FIGS. 2A and 2B, an apparatus for electroporating and/or microporating and electroporating tissue is described. Briefly, the apparatus comprises a heated probe suitable for conducting heat to a surface of the tissue to form at least one micropore therein; at least first and second electrodes spaced apart from each other on the tissue, with the first electrode being electrically coupled to the micropore; and control means for supplying energy to the heated element so as to form the at least one micropore, and for applying electrical voltage between the first and second electrodes for electroporating the tissue.

Specifically, the apparatus, shown generally at reference numeral 200, comprises at least two electrodes 210 and 212. At least one of the electrodes is positioned in one of the micropores M1 and M2 formed through the tissue surface TS, such as skin, and the other electrode is spaced from it and placed on the tissue surface to complete the current path through the tissue. Preferably, the electrodes 210 and 212 are placed in micropores M1 and M2. The electrodes 210 and 212 may be supported by a tissue-contacting layer 214. Electrical voltage is applied between the electrodes 210 and 212 by energy supply means, included as part of a control system 220. The control system 220 includes the appropriate circuitry to supply electrical current and electrical voltage, and to control an optical energy source (if needed). Electrical contact of the electrodes 210 and 212 with the micropores can be achieved with a compliant electrolyte, such as a conductive hydrogel or a saline solution placed on the surface of the tissue in the micropores. Once again, each electrode is preferably positioned proximate a micropore so as to be electrically coupled thereto.

The micropores M1 and M2 are formed prior to energization of the electroporation electrodes 210 and 212. These micropores may be formed in several ways, including thermal ablation via a heated probe by electrical or optical energy. Optical or laser thermal ablation involves placing a photosensitizing assembly, including an optically absorbing compound such as a dye, in contact with the surface of the tissue, optical energy is focused on the photosensitizing assembly which heats it, and the heat is transferred to the surface of the tissue, forming a micropore. The details of this technique are well described in all of the co-pending applications, which are incorporated herein by reference. In this case, a source of optical energy (not shown), controlled by the control system 220, is optically coupled to the photosensitizing assembly placed on the surface of the tissue. Alternatively, the skin could be microporated using a laser which emits at a wavelength which is directly absorbed by the tissue to be removed such as an excimer, holmium, erbium, or CO2 laser or the like. The use of direct laser absorption to form micropores is well known in the art. The application of the electroporation methods to which this invention is directed are suitably compatible with those other methods for forming the micropores in the skin.

In accordance with a preferred embodiment of the present invention, the electrodes 210 and 212 also serve as electrically heated probes used for thermally ablating the tissue to form the micropores M1 and M2. Such electrically heated probes for microporating tissue are disclosed in the aforementioned co-pending U.S. application Ser. No. 08/776,863. Specifically, each electrode 210 and 212 comprises an electrically heated probe consisting of an electrically heated wire which is responsive to electrical current supplied therethrough. As shown in FIG. 2B, during the microporation stage or cycle, electrical current is coupled via conductor leads 222 and 224 to electrode 210 to supply an electrical current therethrough, and electrical current is also coupled via conductor lead lines 226 and 228 to electrode 212. On the other hand, during the electroporation stage or cycle, a voltage is applied to the conductors 222 and 224, relative to a voltage potential applied to conductors 226 and 228, causing electrode 210 to be at a positive potential with respect to electrode 212, or alternatively at a negative potential with respect to electrode 212 (depending on the polarity desired). Thus, the electrically heated probes described above are dual purpose in that they can perform the functions of microporation and of electroporation.

Figure 3:
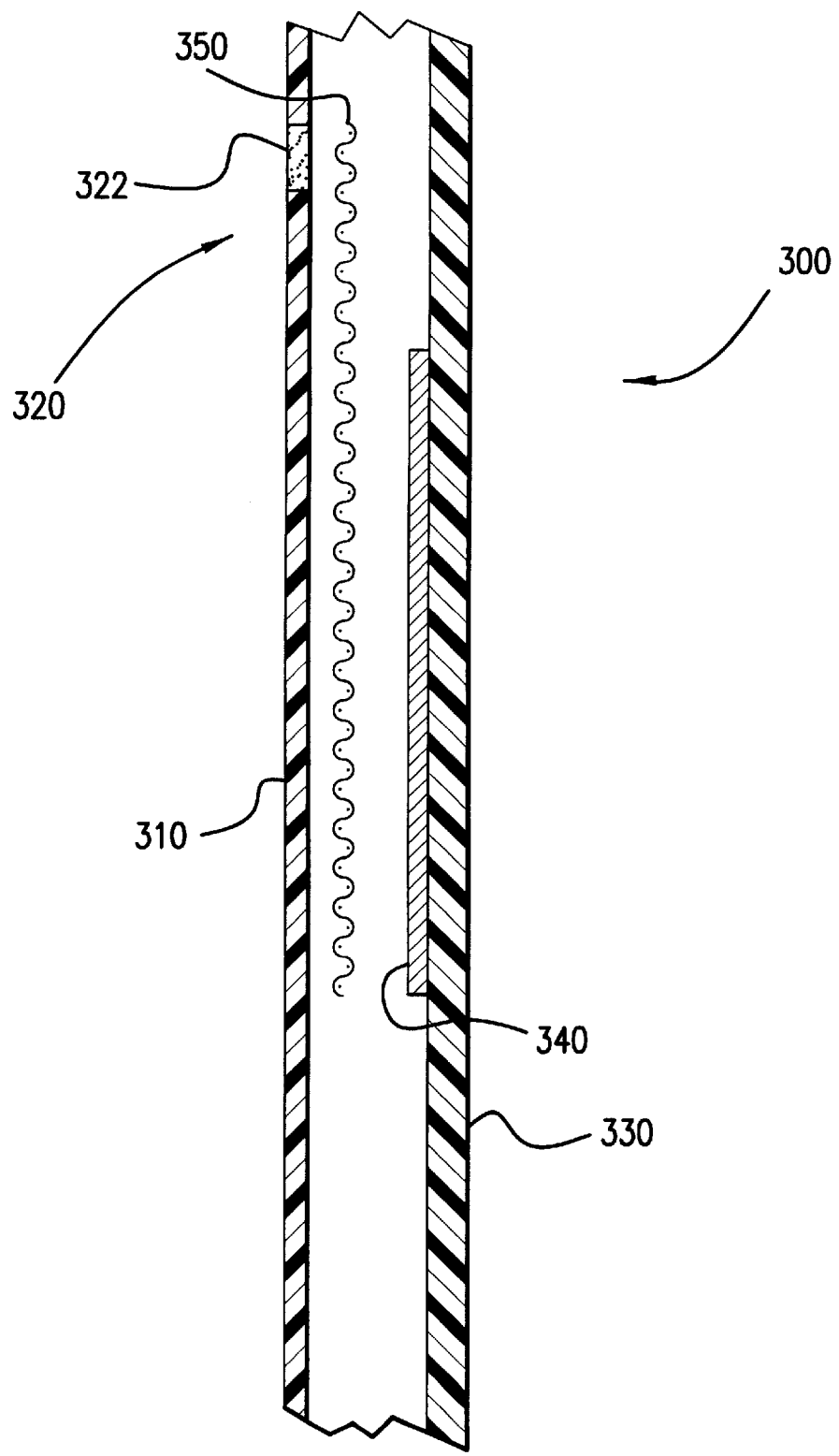
FIG. 3 is an enlarged longitudinal cross-sectional view of a device suitable for use in microporating and electroporating tissue.
Figure 4:
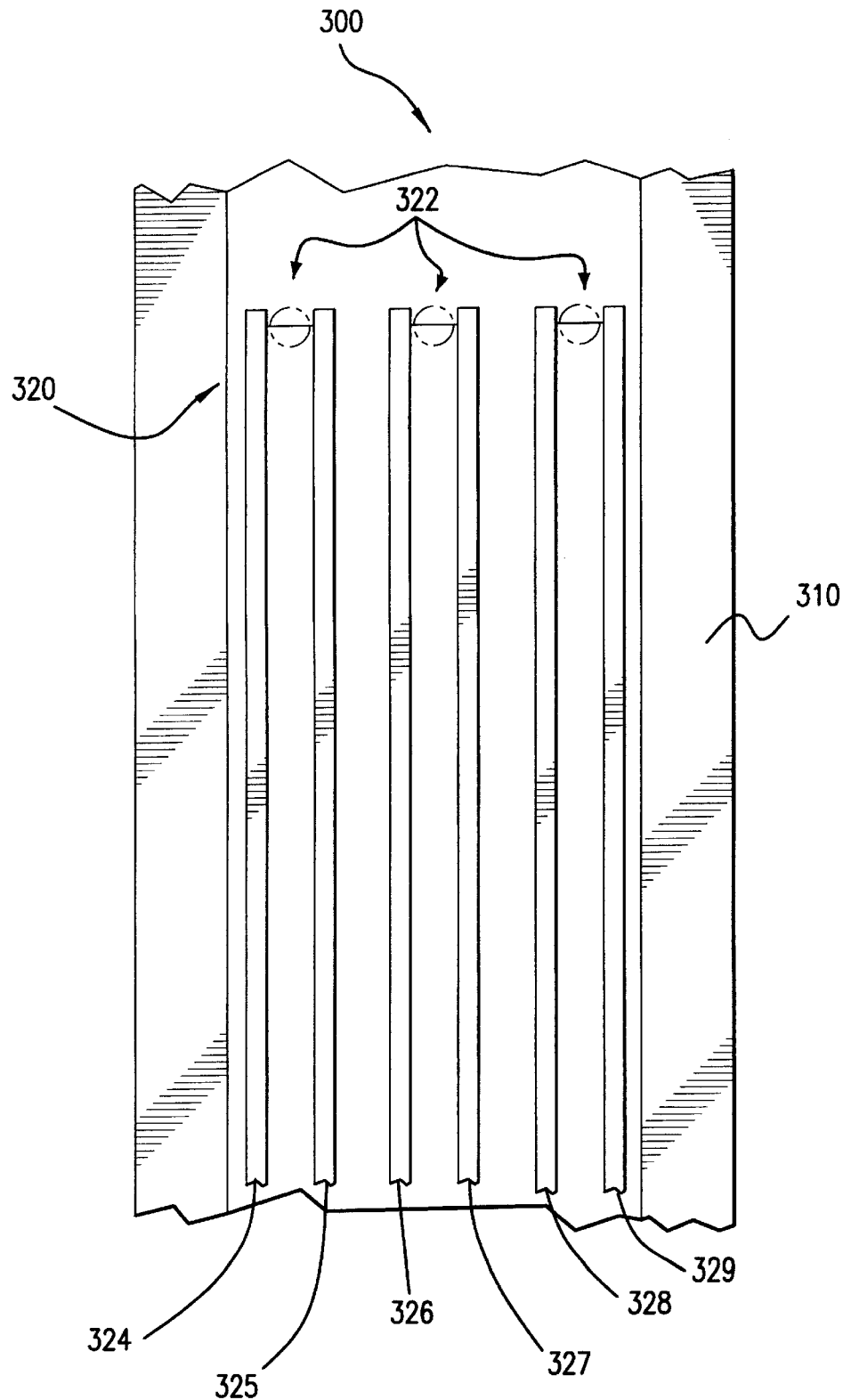
FIG. 4 is a bottom view of the device of FIG. 3, showing the electrically heated probes used for microporating and electroporating tissue.

FIGS. 3 and 4 illustrate the incorporation of dual purpose electrically heated probes as part of an integrated fluid harvesting, collection and analysis device, shown generally at reference numeral 300. The device 300 includes a tissue-contacting layer 310 having an electrically heated probe surface 320. The device 300 further comprises a detecting layer 340 such as a photometric sensor or an electrochemical biosensor, both of which are capable of providing an indication of a characteristic of a collected biological fluid, such as the level of an analyte in interstitial fluid. A meter (not shown) is coupled by a meter-interface layer 330, to the detecting layer 340 either electrically or optically, depending on the type of detecting layer used. The integrated device 300 is more fully disclosed in U.S. application Ser. No. 60/077,135, entitled "Integrated Poration, Harvesting And Analysis Device, And Method Therefor."

As shown in more detail in FIG. 4, the electrically heated probe surface 320 comprises several electrically heated probes 322 provided on the bottom surface of the tissue-contacting layer 310. Three electrical heated probes 322 are shown, but any number of them may be provided. Each of the three heated probes 322 are connected to a pair of the electrical conductors 324, 325, 326, 327, 328 and 329 as shown. The electrical conductors extend the length of the tissue-contacting layer 310 and terminate at a plurality of points near the lower end of the integrated device 300. Each electrically heated probe 322 is connected to a control system by the respective pairs of conductors {324, 325}, {326, 327} and {328, 329} as shown in FIG. 4.

Each electrically heated probe 322 can be activated individually through the appropriate selection and energization of the conductors 324, 325, 326, 327, 328 and 329. It may be advantageous to excite all electrically heated probes 322 simultaneously, thereby enabling either a series or parallel wiring design, reducing the number of interconnections to the device and facilitating a more rapid poration process. If only one electrically heated probe 322 is provided, then at least two conductors are provided for supplying electric current to it.

The electrically heated probes 322 function as solid thermal probes and are electrically heated so that a temperature of the tissue, if skin, is raised to greater than 123 C. The electrically heated probes 322 comprise, for example a 100 to 500 micron long, 50 micron diameter, tungsten wire element. A number of human clinical studies have been performed wherein the surface microporation was achieved by using these types of wires as the electrically heated probe. These tungsten elements are typically laid flat against some form of a backing which naturally limits the depth of penetration of the wire element into the tissue as it is being microporated (by virtue of the size of the element). The temperature of the heated element is modulated as needed to effect the microporation process. Such pulse duty cycle and modulation techniques are disclosed in co-pending U.S. application Ser. No. 08/776,863.

Figure 5:
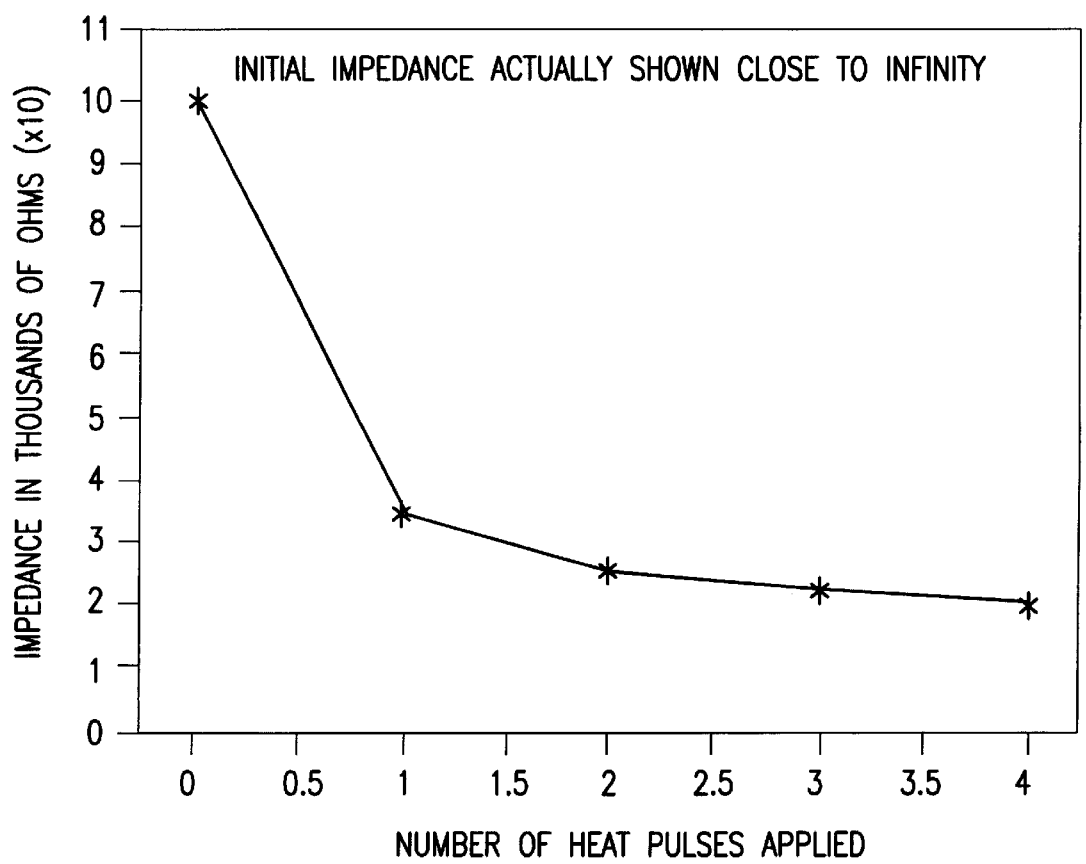
FIG. 5 is a graph showing the electrical impedance between an electrically heated probes after micropores are formed in the skin.

The graph of FIG. 5 shows impedance data between two electrically heated probes (tungsten elements) spaced apart by 2.5 mm on human skin. The graph shows that immediately after even a first pulse is applied, the electrical impedance between them through the body's core drops by several orders of magnitude and then continues to drop with each subsequent pulse as the probe enters deeper into the viable skin tissues, making this an ideal electrode for delivering the desired electroporation pulse. The thermal pulses each reached a maximum of 700° C. and had a duration of 3 ms. The inherent and perfect alignment between the electrically heated probe and the micropore it has created also simplifies the process, requiring no additional steps or hardware to position the electrode.

Moreover, that the electrically heated probes 322 also function as electroporation electrodes is particularly advantageous because they are already contacting the moist viable epidermis after the microporation process has been performed. With these electrodes in place, a mild current, either DC or AC can be established from one or more electrodes to another one or more electrodes, or from one (or more) electrodes to a separate electrode by the application of a suitable voltage between the electrodes, to induce an electromagnetic force field in the ISF-laden tissues beneath the stratum corneum to enhance the outflow of the ISF sample.

A similar technique can be applied with the use of an optically heated probe in an integrated device, such as that disclosed in the co-pending application filed on even date. However, additional electrodes, such as those shown in the device of FIGS. 3 and 4, are additionally required in order to deliver the electroporation energy to the microporated tissue. These additional electrodes can be conveniently formed on the lower surface of the photosensitizing assembly or layer using a lithographic process to create a printed circuit type pattern of conductive traces, portions of which serve as the electrodes on the tissue-contacting side of this layer. This pattern of conductors registers the electrodes to the micropores to be formed, so that at least one electrode in the conductive trace is electrically coupled to a micropore.

Referring back to FIG. 2A, when a voltage is applied between the electrodes, so as to drive a current between them through the tissue, current flux lines EF are created, such that at least one or more of them pass through the intervening targeted tissue structures, such as the capillaries, CP in the tissue. These flux lines (current paths) preferably go as deep as the papillary dermis so as to affect the capillaries therein. The voltage pulsing scheme may consist of a first voltage pulse of a polarity followed by a second voltage pulse of an opposite polarity. This causes current to flow in both directions between the electrodes. An advantage of redirecting the current flow in both directions at a given set of micropores is that by presenting the body with a balanced AC signal, no cumulative electrical polarization is established. This balanced signal has been shown to minimize the sensation to an individual.

Depending on the depth of the micropores and the penetration of the electrodes into them, the tissue may be deformed by a predetermined amount D so as to further increase the number of electric flux lines that pass through specific targeted tissue structures, such as capillaries in the tissue. For example, the tissue may be deformed by as much as 0.5 mm. This deformation could be achieved by several means. For example, the tissue could be simply squeezed together between the microporations.

FIG. 6 illustrates a mechanical element that can be used to impart a bow in the tissue. The mechanical element 400 has a small opening 410 therein (2 mm to 4 mm). Applying force to the mechanical element 400 presses the device onto the skin at the poration site and thus causes the surface of the tissue, i.e., the skin, to bow or bulge into the opening 410 and between the electrodes supported on the device 300. This bulge of the tissue enhances the effect that the current paths created during electroporation can have in the tissue, as shown in FIG. 2. Furthermore, this induces a positive pressure gradient in the ISF, forcing the fluid towards the micropore(s) where it can exit the tissue and enter a fluid management chamber of the device.

FIG. 7 illustrates another means of creating a bulge in the tissue. A vacuum chamber 500 can be created above the surface of the tissue which is to be electroporated, contained by a sealed container. A source or means of negative pressure, such as a pump 510 is coupled to an enclosed chamber which is sealed over the area of the tissue to be treated. The tissue is sucked into the chamber 500 using a mild suction, wherein the dimensions and shape of the opening to the chamber 500 and the amount of suction applied produce the desired amount of deformation of the tissue surface. Other suction means, such as a syringe or diaphragm are also suitable.

The use of electroporation coupled with microporation achieves significant advantages. Specifically, in the case of conventional electroporation, where pulses exceeding 50 to 150 volts are routinely used to electroporate the stratum corneum or mucosal layer, in the microporated tissue environment of the present invention, pulses of only a few volts can be sufficient to electroporate the cell, capillary or other membranes within the targeted tissue. This is principally due to the dramatic reduction in the number of insulating layers present between the electrodes once the outer surface of the tissue has been opened, as reflected by the graph of FIG. 5.

Figure 8:
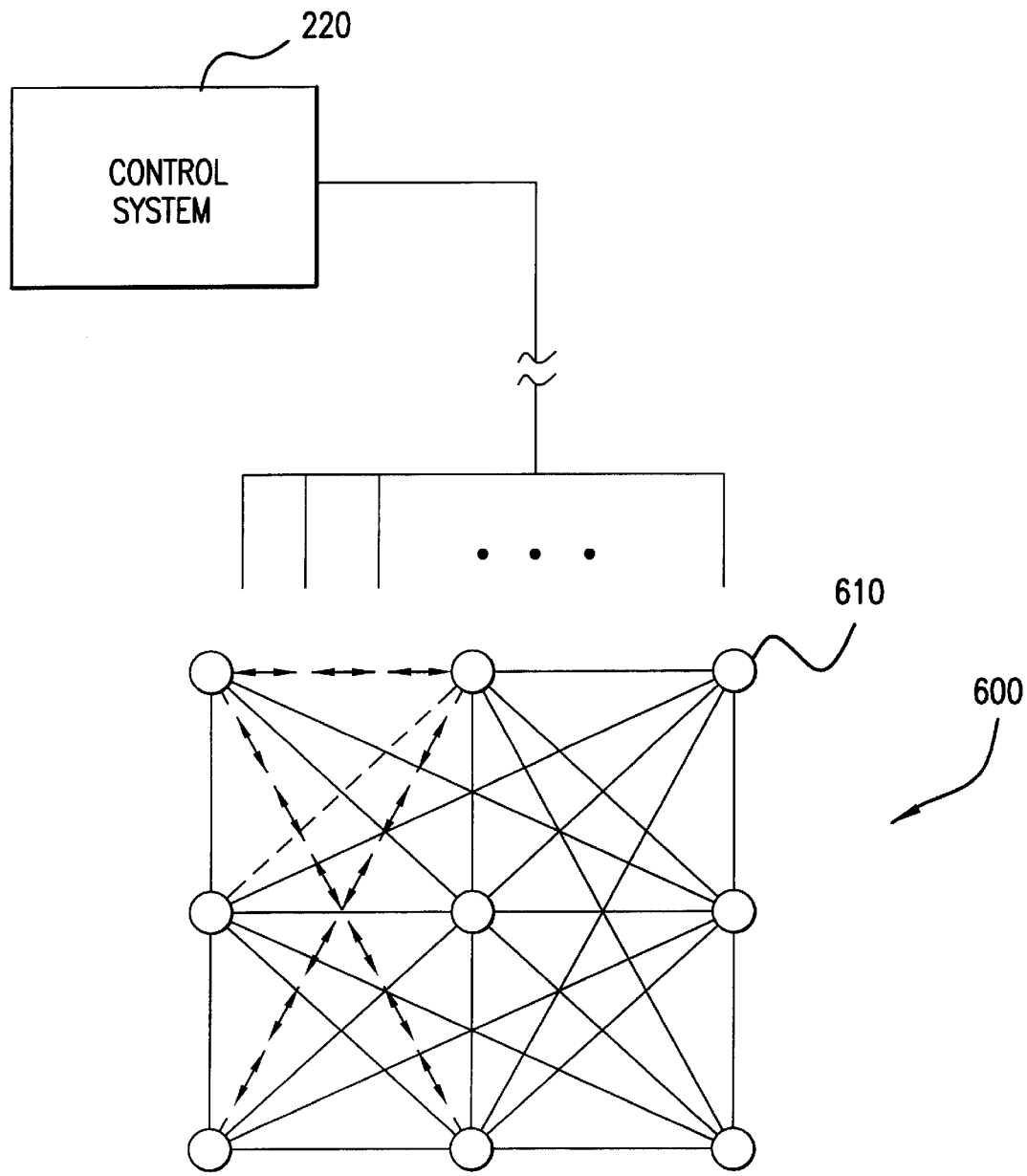
FIG. 8 is a schematic diagram of a multiple electrically heated probe array suitable for microporating tissue and electroporating the tissue in multiple directions.

The manner in which the electroporation pulses are applied may vary. For example, a plurality of micropores spaced apart from each other in the tissue may be formed, and the electrical pulses are then applied in multiple directions between different sets (pairs or more) of electrodes to facilitate the electroporation of a larger percentage of the area of the targeted structures in the intervening tissue such as capillary walls. This multi-directional cross firing can be achieved with a plurality of electrically heated probes, similar to those shown in FIGS. 3 and 4. FIG. 8 illustrates such an embodiment, in which an 3×3 array 600 of electrically heated probes 610 is applied to the surface of the tissue. The electrically heated probes 610 also serve as the electroporation electrodes. The array can be formed using well known circuit printing technologies, such as etching, lithographic film deposition, etc. A suitable electrically heated poration element is then placed onto the appropriate conductors etched onto a circuit board/substrate. In this embodiment, all or selected ones of the heated probes 610 are energized to form micropores in the tissue. Then, sets of the heated probes 610, which are already suitably electrically coupled to their respective micropores, are connected to a source of AC or DC voltage to create a current distribution between them. Voltage is applied between different sets of poration elements, now acting as electroporation electrodes, at the different micropores so as to change the direction of the electroporation through the tissue. Successive pulses are preferably either in an opposite polarity with respect to the same set of electrodes and/or are between different sets of electrodes. Each possible path can be energized in either polarity, or toggled back and forth between polarities. The advantages of redirecting the current flow in both directions at a given set of micropores is that by presenting the body with a balanced AC signal, no cumulative electrical polarization is established. Furthermore, this multi-directional current control has been shown to dramatically reduce the sensation of the subject during the electroporation process as has the setting of the pulse parameters below certain peak voltage levels and with a duration of each pulse kept to a minimum, preferably under a few milliseconds.

It is well known in the art that electroporation can cause openings to form, temporarily, in the cell membranes and other internal tissue membranes. By having breached the surface of the tissue, such as the stratum corneum, mucosal layer or outer layer of a plant, and if desired the epidermis and dermis, or deeper into a plant, electroporation can be used with parameters tailored to act selectively on these underlying tissue barriers. For any electromagnetic energy enhancement means, the specific action of the enhancement can be designed to focus on any part of the micropore, e.g., on the bottom of the micropore by focusing the discharge of the electrodes, phasing of multiple electrodes or other field forming methods and devices and the like. Alternatively, the enhancement can be focused more generally on the entire micropore or the area surrounding the pore.

The mode of operation of electroporation when applied after the microporation of the tissue, has the advantage of being able to use operational parameters which would be useless for un-microporated, intact tissue surface conditions. In particular, the operational settings useable when applied after the microporation of the skin or mucosal layer or the outer layer of a plant are generally close to those typically used in in vitro applications where single cell membranes are opened up for the delivery of a substance. Examples of these parameters are well known in the literature. For example, Sambvrook et al., Molecular Cloning: A Laboratory Manual, 2d Ed., Cold Spring Harbor Laboratory, Cold Spring Harbor, N.Y., 1989.

Still another enhancement which may be used in conjunction with the electroporation techniques described herein is the application of sonic energy. Suitable sonic energy techniques are described in the aforementioned co-pending applications.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for electroporating tissue, comprising the steps of:

forming at least one micropore to a predetermined depth through a surface of the tissue;

positioning at least a first electrode on the surface of the tissue electrically coupled to the at least one micropore and a second electrode on the surface of the tissue spaced apart from the first electrode; and applying an electrical voltage between the first and second electrodes to produce a desired electroporation in the tissue.

2. The method of claim 1, wherein the step of applying electrical voltage comprises applying an electrical voltage of a sufficient magnitude between the first and second electrodes suitable to produce a potential drop exceeding a nominal threshold to achieve electroporation across the epithelial cell layer but not sufficient to electroporate membranes present in other tissue structures thereby achieving a selective electroporation of targeted membranes.

3. The method of claim 1, wherein the step of forming comprises forming first and second micropores spaced apart from each other, and wherein the first electrode is positioned to be electrically coupled to the first micropore, and the second electrode is positioned to be electrically coupled to the second micropore.

4. The method of claim 1, wherein the step of applying electrical voltage comprises applying a voltage pulse of a first polarity with respect to the first and second electrodes, followed by a voltage pulse of an opposite polarity with respect to the first and second electrodes.

5. The method of claim 1, wherein the step of forming comprises forming a plurality of micropores spaced apart from each other in the tissue, and the step of positioning comprises placing a plurality of electrodes each being electrically coupled to a different one of the micropores, and wherein the step of applying electrical voltage comprises applying electrical voltage pulses between different sets of the plurality of electrodes so as to electroporate the tissue in multiple directions.

6. The method of claim 5, wherein the step of applying comprises applying a voltage pulse of a first polarity between a first set of electrodes followed by a voltage pulse of an opposite polarity between the first set of electrodes.

7. A method of collecting biological fluid from the tissue comprising the steps of claim 1, and further comprising collecting biological fluid from the tissue through the at least one micropores.

8. The method of claim 7, and further comprising analyzing the biological fluid with a biosensor.

9. The method of claim 8, wherein the step of analyzing comprises determining a concentration of an analyte in the biological fluid.

10. The method of claim 1, wherein the step of forming the at least one micropore comprises applying a photosensitizing material to the surface of the tissue and irradiating the photosensitizing material with optical energy, whereby the photosensitizing material is responsive to the optical energy so as to heat up and conductively transfer heat to the surface of the tissue to form the at least one micropore.

11. The method of claim 1, and further comprising the step of deforming the surface of the tissue between the first and second electrodes so that the surface of the tissue sufficiently bulges between the first and second electrodes to place tissue structures desired to be electroporated in a principal current path between the first and second electrodes.

12. The method of claim 11, wherein the step of deforming comprises mechanically deforming the surface of the tissue.

13. The method of claim 11, wherein the step of deforming comprises applying suction to the surface of the tissue.

14. The method of claim 1, and further comprising the step of delivering a substance to the tissue at the at least two micropores formed therein.

15. The method of claim 1, wherein the step of forming the at least one micropore comprises applying a photosensitizing material to the surface of the tissue and irradiating the photosensitizing material with optical energy, whereby the photosensitizing material is responsive to the optical energy so as to heat up and conductively transfer heat to the surface of the tissue to form the at least one micropore, whereby the step of positioning the first and second electrodes comprises positioning conductive traces on a tissue-contacting side of the photosensitizing material registered with the micropores.

16. The method of claim 1, and further comprising the step of delivering a permeant into the tissue through the at least one micropore.

17. The method of claim 16, and further comprising the step of delivering a permeant into the tissue so as to cause the permeant to pass through the tissue structures that are electroporated.

18. A method for electroporating tissue, comprising the steps of:

forming at least one micropore to a predetermined depth through a surface of the tissue by placing an electrically heated probe at the surface of the tissue and supplying electrical current to the electrically heated probe so as to ablate the surface of the tissue in order to form the at least one micropore;

positioning at least a first electrode electrically coupled to the at least one micropore and a second electrode spaced apart from the first electrode; and applying an electrical voltage between the first and second electrodes to produce a desired electroporation in the tissue.

19. The method of claim 18, wherein the electrically heated probe also serves as the first electrode such that the electrical voltage is applied between the electrically heated probe and the second electrode.

20. A method for electroporating tissue, comprising the steps of:

forming at least one micropore to a predetermined depth through a surface of the tissue by placing first and second electrically heated probes at the surface of the tissue spaced apart from each other and supplying electrical current to each of the first and second electrically heated probes so as to ablate the surface of the tissue in order to form two micropores spaced apart from each other;

positioning at least a first electrode electrically coupled to the at least one micropore and a second electrode spaced apart from the first electrode;

applying an electrical voltage between the first and second electrodes to produce a desired electroporation in the tissue.

21. The method of claim 20, wherein the first and second electrically heated probes further serve as the first and second electrodes such that the electrical voltage is applied between the first and second electrically heated probes.

22. An apparatus for microporation and electroporation of tissue, comprising:

(a) a heated probe suitable for conducting heat to a surface of the tissue to form at least one micropore therein;

(b) at least first and second electrodes suitable for being spaced apart from each other on the tissue; and (c) control means for supplying energy to the heated probe so as to cause formation of the at least one micropore in the tissue, and for applying an electrical voltage between the first and second electrodes suitable for electroporating the tissue.

23. The apparatus of claim 22, wherein the control means supplies a magnitude of electrical voltage applied between the first and second electrodes suitable to produce a potential drop exceeding a nominal threshold to achieve electroporation across the epithelial cell layer but not sufficient to electroporate membranes present in other tissue structures thereby achieving a selective electroporation of targeted membranes.

24. The apparatus of claim 22, wherein the heated probe forms first and second micropores spaced apart from each other in the tissue, and wherein the first electrode is suitable for being electrically coupled to the first micropore and the second electrode is suitable for being electrically coupled to the second micropore.

25. The apparatus of claim 22, wherein the heated probe is an electrically heated probe, and wherein the control means supplies electrical current to the electrically heated probe to form the at least one micropore.

26. The apparatus of claim 25, wherein the electrically heated probe also serves as the first electrode such that the electrical voltage is applied between the electrically heated probe and the second electrode.

27. The apparatus of claim 22, wherein the heated probe comprises first and second electrically heated probes spaced apart from each other each responsive to electrical current supplied by the control means to form two micropores in the tissue spaced apart from each other.

28. The apparatus of claim 27, wherein the first and second electrically heated probes further serve as the first and second electrodes, the control means being coupled to the first and second electrically heated probes so as to apply the electrical voltage therebetween.

29. The apparatus of claim 28, and further comprising a tissue-contacting layer supporting the first and second electrically heated probes, and further comprising conductor means for coupling electrical current from the control means to the first and second electrically heated probes, and for applying the electrical voltage between the first and second electrically heated probes.

30. The apparatus of claim 22, wherein the control means applies a first voltage pulse of a first polarity with respect to the first and second electrodes, followed by a voltage pulse of an opposite polarity with respect to the first and second electrodes.

31. The apparatus of claim 22, and comprising a plurality of electrically heated probes each responsive to electrical current and suitable for forming a plurality of micropores spaced apart from each other in the tissue, and wherein the control means applies electrical voltage pulses between different sets of the plurality of electrically heated probes so as to electroporate the tissue in multiple directions.

32. The apparatus of claim 31, wherein the control means applies a voltage pulse of a first polarity between a first set of electrodes followed by a voltage pulse of an opposite polarity between the first set of electrodes.

33. The apparatus of claim 22, and comprising an integrated device for harvesting and analyzing biological fluid, the integrated device comprising a tissue-contact layer and a detecting layer, wherein the heated probe and the first and second electrodes are supported by the tissue-contacting layer, the detecting layer being positioned adjacent the tissue-contacting layer for detecting a characteristic of a biological fluid collected from the tissue through the at least one micropore.

34. The apparatus of claim 33, wherein the detecting layer comprises an electrochemical biosensor.

35. The apparatus of claim 33, wherein the detecting layer comprises a photometric sensor.

36. The apparatus of claim 22, and further comprising a mechanical element suitable for causing the surface of the tissue to sufficiently bulge between the first and second electrodes to place tissue structures desired to be electroporated in a principal current path between the first and second electrodes.

37. The apparatus of claim 22, and further comprising means for applying suction to the tissue so as to suck the surface of the tissue between the first and second electrodes.

38. A method for electroporating tissue, comprising the steps of:

forming at least one micropore to a predetermined depth through a surface of the tissue;

positioning at least a first electrode electrically coupled to the at least one micropore and a second electrode spaced apart from the first electrode; and applying a voltage pulse of a first polarity with respect to the first and second electrodes, followed by a voltage pulse of an opposite polarity with respect to the first and second electrodes to produce a desired electroporation in the tissue.

39. A method of collecting biological fluid from tissue, comprising the steps of:

forming at least one micropore to a predetermined depth through a surface of the tissue;

positioning at least a first electrode electrically coupled to the at least one micropore and a second electrode spaced apart from the first electrode;

applying an electrical voltage between the first and second electrodes to produce a desired electroporation in the tissue; and collecting biological fluid from the tissue through the at least one micropores.

40. The method of claim 39, and further comprising the step of analyzing the biological fluid.

41. The method of claim 40, wherein the step of analyzing comprises determining a concentration of an analyte in the biological fluid.

42. A method for electroporating tissue, comprising the steps of:

forming at least one micropore to a predetermined depth through a surface of the tissue, wherein the step of forming the at least one micropore comprises applying a photosensitizing material to the surface of the tissue and irradiating the photosensitizing material with optical energy, whereby the photosensitizing material is responsive to the optical energy so as to heat up and conductively transfer heat to the surface of the tissue to form the at least one micropore;

positioning at least a first electrode electrically coupled to the at least one micropore and a second electrode spaced apart from the first electrode; and applying an electrical voltage between the first and second electrodes to produce a desired electroporation in the tissue.

43. A method for electroporating tissue, comprising the steps of:

forming at least one micropore to a predetermined depth through a surface of the tissue;

positioning at least a first electrode electrically coupled to the at least one micropore and a second electrode spaced apart from the first electrode;

applying suction to the surface of the tissue to deform the surface of the tissue between the first and second electrodes so that the tissue bulges between the first and second electrodes; and applying an electrical voltage between the first and second electrodes to produce a desired electroporation in the tissue.

* * * * *